United States Patent [19]
Kahn et al.

[11] Patent Number: 5,873,836
[45] Date of Patent: Feb. 23, 1999

[54] BLOOD PRESSURE MONITORING WITH IMPROVED NOISE REJECTION

[75] Inventors: Alan R. Kahn, Minneapolis, Minn.; Dennis E. Bahr, Middleton, Wis.; Kurt W. Allen, Minneapolis, Minn.

[73] Assignee: BP Sure, LLC, Middleton, Wis.

[21] Appl. No.: 890,402

[22] Filed: Jul. 9, 1997

[51] Int. Cl.⁶ .................................................. A61B 5/00
[52] U.S. Cl. ...................... 600/493; 600/494; 600/490
[58] Field of Search ................................... 600/490, 485, 600/493–6, 500

[56] References Cited

U.S. PATENT DOCUMENTS

| | | |
|---|---|---|
| 3,773,033 | 11/1973 | Rodbard et al. . |
| 3,953,794 | 4/1976 | Moore . |
| 4,005,701 | 2/1977 | Aisenberg et al. . |
| 4,165,491 | 8/1979 | Geffon . |
| 4,245,648 | 1/1981 | Trimmer et al. . |
| 4,313,445 | 2/1982 | Georgi . |
| 4,396,018 | 8/1983 | Sibley . |
| 4,408,614 | 10/1983 | Weaver et al. . |
| 4,592,365 | 6/1986 | Georgi . |
| 4,649,929 | 3/1987 | Weaver et al. . |
| 4,819,654 | 4/1989 | Weaver et al. . |
| 4,840,181 | 6/1989 | Yamaguchi . |
| 4,938,277 | 7/1990 | Niwa et al. . |
| 5,031,630 | 7/1991 | Hirano et al. . |
| 5,135,003 | 8/1992 | Souma . |
| 5,337,750 | 8/1994 | Walloch . |
| 5,392,781 | 2/1995 | Phillipps et al. . |
| 5,482,036 | 1/1996 | Diab et al. . |
| 5,490,505 | 2/1996 | Diab et al. . |
| 5,649,535 | 7/1997 | Voith ....................................... 600/493 |

OTHER PUBLICATIONS

Kim–Gau Ng & Carolyn F. Small, "Survey of Automated Noninvasive Blood Pressure Monitors", J. Clinical Engineering, vol. 19, No. 6, pp. 452–475, Nov./Dec. 1994.

U.S. Patent Appl. S.N. 08/665,286, Method and Apparatus For Detecting Blood Pressure By Blood Pressure Sounds In The Presence of Significant Noise, by Alan R. Kahn, Dennis E. Bahr, and Kurt W. Allen, filed Jun. 17, 1996, notice of allowance mailed Apr. 25, 1997.

U.S. Patent Appl. S.N. 08/665,362, Coherent Pattern Identification In Non–Stationary Periodic Data and Blood Pressure Measurement Using Same, by Alan R. Kahn, Dennis E. Bahr, and Kurt W. Allen, filed Jun. 17, 1996.

Bernard Widrow, et al., "Adaptive Nosie Cancelling: Principles and Applications", IEEE Proceedings, vol. 63, No. 13, pp. 1692, 1710–1711, Dec. 1975.

*Primary Examiner*—Robert L. Nasser
*Attorney, Agent, or Firm*—Foley & Lardner

[57] ABSTRACT

A method and apparatus is provided for distinguishing blood pressure sounds from noise in an automatic blood pressure monitoring system using the information contained in two microphone signals. Two microphones are placed on a patient along an axis of an artery to pick up blood pressure sounds. Pressure is applied to the artery such that the artery opens and closes during each heart cycle, the opening snap of the artery producing a blood pressure sound. The two microphone signals are sampled, filtered, and multiplied together to produce a microphone signal product. The microphone signal product is wave width filtered to remove therefrom portions of the signal having a wave width which is less than a selected minimum wave width value. A blood pressure sound is indicated as being detected when an amplitude of this wave width filtered microphone signal product exceeds a noise signal threshold level. The microphone signal product is also wave width filtered to remove therefrom portions of the signal having a wave width which is greater than a selected maximum wave width value. The amplitude of the resulting noise amplitude signal is used to adjust dynamically the noise signal threshold level in response to changing noise conditions. The detection of blood pressure sounds at a range of applied pressure levels is used to determine the systolic and diastolic blood pressure levels of the patient.

53 Claims, 5 Drawing Sheets

BLOOD PRESSURE MONITORING WITH IMPROVED NOISE REJECTION

FIELD OF THE INVENTION

This invention pertains generally to the field of blood pressure monitoring methods and devices, and more particularly to blood pressure monitoring systems employing one or more microphones for detecting the onset and disappearance of blood pressure sounds as pressure is applied to the brachial artery of a patient, and methods and devices for reducing the effect of noise on such systems.

BACKGROUND OF THE INVENTION

A common method for measuring the blood pressure of a patient employs an inflatable cuff (sometimes referred to as a Riva-Rocci cuff) wrapped around the upper arm of the patient whose blood pressure is to be determined. As the cuff is inflated, the cuff pressure, and the pressure applied to the arm of the patient, increases. As the pressure applied to the arm is increased beyond the highest blood pressure level in a brachial artery located in the arm beneath the cuff, the artery is forced closed.

The blood pressure in the brachial artery is not constant, but varies with time in relation to the beating of the heart. Following a contraction of the heart to pump blood through the circulatory system, the blood pressure first increases to a maximum level, then reduces to a minimum level. The maximum blood pressure level between heart beats is known as the systolic blood pressure level. The minimum blood pressure level between heartbeats is known as the diastolic blood pressure level.

As the pressure in the inflatable cuff is reduced from a high level above the systolic blood pressure level, where the brachial artery is forced permanently closed, to a pressure level below the systolic blood pressure level, the brachial artery beneath the cuff will begin to open and close with each heart beat as the blood pressure level first exceeds the cuff pressure, and then falls below the cuff pressure. The arterial wall acts in a non-linear fashion with respect to the blood pressure level. Thus, as the blood pressure exceeds the cuff pressure, the artery will literally "snap" open, producing a low frequency blood pressure sound. This blood pressure sound may be detected using a microphone placed under the cuff against the patient's arm. The turbulent flow of blood through the artery following the opening snap also produces sounds, known as Korotkoff sounds, that may be detected using a stethoscope or microphone placed near the downstream end of the cuff on the patient's arm. The highest cuff pressure at which Korotkoff sounds or blood pressure sounds are detectible thus corresponds to the systolic blood pressure level of the patient.

As the cuff pressure is gradually reduced further, the cuff pressure will be brought below the diastolic blood pressure level through a gradual pressure change. At this pressure level, the brachial artery beneath the cuff remains open throughout the heartbeat cycle. Blood pressure sounds, caused by the opening of the artery, and Korotkoff sounds, will, therefore, not be produced. The lowest cuff pressure at which blood pressure sounds or Korotkoff sounds can be detected thus corresponds to the diastolic blood pressure level of the patient. The determination of blood pressure levels in this manner, based on the detection of the onset and disappearance of Korotkoff sounds or blood pressure sounds as varying pressures are applied to an artery, is known as an auscultatory method of blood pressure determination.

In manual auscultatory blood pressure measurement methods, a stethoscope is used to detect the onset and disappearance of Korotkoff sounds. Thus, manual blood pressure measurements are highly dependent on the skill and hearing ability of the person taking the measurement. To overcome this dependence on human skill and judgment, and to automate the process of determining a patient's blood pressure, automatic blood pressure monitoring systems based on the auscultatory method of blood pressure determination have been developed. These automatic systems employ one or more microphones placed in or under an automatically inflatable and deflatable cuff to detect blood pressure sounds. However, movement of the patient, such as during exercise, vibration during transport, and other activity around the patient, will cause noise to be picked up by the blood pressure monitor microphones along with the blood pressure sounds. The automatic blood pressure monitoring system must, therefore, be able to separate the noise from the blood pressure sounds in order to accurately determine the patient's blood pressure levels. This has been achieved, for example, by filtering the microphone signal using a band pass filter whose pass band corresponds to a known frequency range of blood pressure sounds. This eliminates much of the noise from the microphone signal.

Some automatic blood pressure monitoring systems employ two microphones for detecting blood pressure sounds. For example, two microphones may be placed under the inflatable cuff separated by a distance such that a low frequency blood pressure sound will reach the first microphone approximately 180°, but at least more than 90°, out of phase from the second microphone. Noise signals will tend to reach each microphone essentially simultaneously, and in phase. Therefore, subtracting the two microphone signals from each other will tend to enhance the useful data and diminish unwanted noise. The two microphone signals can be added and subtracted from each other to create signal and noise detection thresholds. Microphone signals are considered to be valid blood pressure sound detections if they meet the detection thresholds.

Another method that makes use of two microphones relies on using a first microphone placed on the arm of the patient upstream from a second microphone to provide a time gate for the second microphone. Once again, this method relies on the fact that blood pressure sounds will propagate down the arm of the patient from the first microphone to the second microphone, whereas a noise signal will likely be picked up by both microphones simultaneously. When a sound signal exceeding a certain threshold is picked up by the first microphone, a time gate is opened which causes the downstream microphone to "listen" during a time interval a few milliseconds later, corresponding to the estimated propagation time of a blood pressure sound between the two microphones. If a sound signal is picked up by the second microphone during the gate period, the signal may be considered a valid blood pressure sound detection. A similar gating scheme may be used for blood pressure monitors employing a single microphone. Since the time delay between the contraction of the heart and the appearance of a blood pressure sound at a microphone placed on the arm of a patient can be estimated, the signal from a ECG heart monitor may be used to generate a delayed gate for the blood pressure monitor microphone. A sound signal picked up by the microphone during the gate period may be considered a valid blood pressure sound detection.

An effective automatic blood pressure monitoring system and method is described in pending U.S. patent application Ser. No. 08/665,286, entitled "Method and Apparatus for Detecting Blood Pressure by Blood Pressure Sounds in the Presence of Significant Noise", filed Jun. 17, 1996, by the inventors of the present invention. This method for accurately detecting the blood pressure sounds produced by the opening snap of a patient's artery in the presence of significant noise levels uses the phase information contained in two microphone signals. Two microphones are placed on a patient along the axis of an artery, with their centers separated by a distance such that blood pressure sounds picked up by each of the microphones will be approximately 180°, but at least more than 90°, out of phase with each other. Noise picked up by the microphones will typically be in phase. The two microphone signals are filtered using band pass filters having pass bands corresponding to the frequency range of the blood pressure sounds. This removes some of the noise from the microphone signals. The filtered microphone signals are then sampled and multiplied together, or convolved in the frequency domain, to generate a microphone signal product. If the microphone signal product is negative, indicating that the microphone signals are out of phase at the sample time, the detection of a valid blood pressure signal for that sampling time is indicated. A selected number of consecutive valid blood pressure signal detections indicates the detection of a blood pressure sound. The detection of blood pressure sounds at a range of cuff pressures is used to determine the systolic and diastolic blood pressure levels of the patient. This blood pressure monitoring method enables accurate blood pressure measurements to be made during the extremes of noise interference encountered during patient movement, shivering, or exercise, or caused by ambient vibrations encountered in highly noisy environments. However, even this highly effective method for monitoring blood pressure may be improved. Since this method relies on the phase information, rather than the amplitude information, contained in the two microphone signals, a false blood pressure sound detection may be indicated in certain situations. For example, if two independent noise signals are separated in time by an amount corresponding to the expected phase difference of the blood pressure sounds, the product of the two microphone signals will be negative, and the detection of a blood pressure sound may be erroneously indicated. This may occur even if the amplitude of the noise signals is relatively low.

SUMMARY OF THE INVENTION

The present invention provides a method and apparatus for accurate automatic blood pressure monitoring in noisy environments. In accordance with the present invention, blood pressure monitoring accuracy is improved by an improved method of distinguishing microphone signals indicative of blood pressure sounds from noise. The present invention employs two microphones to detect blood pressure sounds. The microphones are preferably placed on a patient and separated from each other by a distance such that a blood pressure sound will be picked up by a first microphone more than 90°, and preferably approximately 180°, out of phase with respect to the blood pressure sound picked up by the second microphone. The two microphone signals are preferably filtered, and then multiplied together to form a microphone signal product. The microphone signal product is provided to a blood pressure sound detection data stream. A wave width filter is applied to the microphone signal product in the blood pressure sound detection data stream to remove from the microphone signal product all portions therefore having a wave width, e.g., from zero crossing to zero crossing, which is less than a selected minimum wave width value. The minimum wave width value is preferably selected to be shorter than the expected wave width of a blood pressure sound signal. Thus, the output of the wave width filter in the blood pressure sound detection data stream is a wave width filtered blood pressure sound detection signal which includes all portions of the microphone signal product which correspond to blood pressure sounds, with some of the noise removed therefrom. The wave width filtered blood pressure sound detection signal is compared to a noise signal threshold level. If the wave width filtered blood pressure sound detection signal exceeds the noise signal threshold level, a blood pressure sound detection is indicated.

The noise signal threshold level is preferably adjusted in response to changing noise conditions based on the microphone signal product which is provided to a noise signal threshold level data stream. The microphone signal product provided to the noise signal threshold level data stream is filtered by a wave width filter which removes all portions of the microphone signal product having a wave width, e.g., from zero crossing to zero crossing, that is greater than a selected maximum wave width value. The maximum wave width value is selected such that the output of the wave width filter in the noise signal threshold level data stream is a wave width filtered noise amplitude signal which is all noise. The selected maximum wave width value may be set equal to the selected minimum wave width value for this purpose. The wave width filtered noise amplitude signal is compared to a previously established noise signal threshold level. If the wave width filtered noise amplitude signal exceeds the noise signal threshold level, the noise signal threshold level is increased by an amount related to the product of a first noise signal threshold level adjustment coefficient and the difference between the wave width filtered noise amplitude signal and the previous noise signal threshold level. If the wave width filtered noise amplitude signal is less than the noise signal threshold level, the noise signal threshold level is reduced by an amount related to the product of a second noise signal threshold level adjustment coefficient and the difference between the wave width filtered noise amplitude signal and the previous noise signal threshold level. Thus, the noise signal threshold level is increased in response to increasing noise conditions and decreased when noise levels decrease. Preferably, the first and second noise signal threshold level adjustment coefficients are selected such that the noise signal threshold level is increased rapidly in response to increasing noise levels, but decreased slowly in response to decreasing noise levels.

The present invention may preferably be used in an automatic blood pressure monitoring system employing an inflatable cuff that is wrapped around the arm of a patient whose blood pressure is to be monitored. The two microphones are placed under the cuff against the patient's arm. The microphones are preferably fixed within the cuff near the center of the cuff, and are placed along the axis of a brachial artery. The centers of the two microphones are separated by a distance such that a blood pressure sound signal picked up by one of the microphones will be picked up out of phase (preferably approximately 180°, but at least 90° or more, out of phase) at the second microphone. The pressure in the inflatable cuff may be controlled by a pressure controller, including a pump and one or more valves, that is capable of inflating the cuff to a pressure level above the maximum probable systolic blood pressure level of the patient and of gradually lowering the pressure in the cuff from this high pressure level to a pressure level below the diastolic blood pressure level of the patient at which blood pressure sounds are no longer detected. A pressure transducer in the cuff or pressure controller is employed to determine the amount of pressure in the cuff. The pressure transducer signal is preferably converted to a digital signal for storage and use by a digital microprocessor based system controller that is used to control the pressure controller and to determine the patient's blood pressure levels based on the pressure transducer output and the blood pressure sounds detected by the microphones. The signals from the two microphones are preferably filtered to select the frequencies or other characteristics of the microphone signals which correspond to blood pressure sounds produced by the opening of the brachial artery. This may be accomplished using band pass filters. The desired band width is in the range of approximately 15 Hz to 45 Hz. The two microphone signals may also be filter processed by gain controlling one of the microphone signals to match the other microphone signal, adding the matched microphone signals together to remove the blood pressure sound component from the signals, and subtracting the resulting noise signal from each of the microphone signals to reduce the noise component in the microphone signals.

The filtered microphone signals are preferably converted to digital signals that are provided to the digital microprocessor based system controller, which multiplies the two microphone signals together to form the microphone signal product. The two microphone signals are preferably sampled at a relatively high rate (500 Hz–2,000 Hz). At each sample time, a value corresponding to the state (amplitude and sign) of each filtered microphone signal is determined and the two signals are multiplied together. The microphone signal product may thus be generated directly, in a conventional manner, in the time domain, or the two microphone signals may be converted to the frequency domain using a fast Fourier or sliding Fourier transform, and then convolved to produce the microphone signal product.

Processing of the microphone signal product in blood pressure sound detection and noise signal threshold level data streams, including wave width filtering of the data streams, comparison of the wave width filtered blood pressure sound detection signal with the noise signal threshold level to indicate the detection of a blood pressure sound, and modification of the noise signal threshold level in response to changing noise conditions, may preferably be implemented in the system microprocessor. The system microprocessor may be programmed to monitor the microphone signals for the occurrence of blood pressure sound detections at cuff pressure levels ranging from above the maximum expected systolic blood pressure level of a patient to below the minimum expected diastolic blood pressure level of the patient. The highest cuff pressure at which a blood pressure sound detection is indicated in accordance with the present invention may be displayed to a user of the system as the systolic blood pressure level of the patient. The lowest cuff pressure at which a blood pressure sound detection is indicated in accordance with the present invention may be displayed to the user as the diastolic blood pressure level of the patient. Blood pressure monitoring using this method of the present invention may be accomplished during a gradual decrease in cuff pressure, from above the systolic to below the diastolic pressure level, or during a gradual increase in cuff pressure, from below the diastolic to above the systolic pressure level.

Blood pressure sound detection with improved noise rejection in accordance with the present invention may be used in combination with various blood pressure monitoring systems or methods to improve the accuracy of such systems or methods. For example, the present invention may conveniently be combined with the blood pressure monitoring system previously described wherein the phase information contained in two microphone signals is used to distinguish blood pressure sound detections from noise. In combination with such a blood pressure monitoring system, the present invention may be employed as a second check for verifying the results obtained by the phase only based system. Thus, in accordance with the present invention, the detection of a blood pressure sound may preferably be indicated only when the microphone signal product is both negative and exceeds a noise signal threshold level as established in accordance with the present invention. The effectiveness of the blood pressure monitoring system in distinguishing blood pressure sounds from noise in highly noise environments may thus be improved by the combined use of both the amplitude and phase information contained in the microphone signals.

Blood pressure monitoring in accordance with the present invention provides for the accurate detection of blood pressure sounds and measurement of blood pressure levels in the presence of significant noise levels. Improved noise rejection in accordance with the present invention may be employed as the central mechanism for distinguishing blood pressure sounds from noise in an automatic blood pressure monitoring system, or may be employed in combination with other blood pressure monitoring systems to improve the performance thereof. The present invention features dynamic adjustment of a noise signal threshold level in response to changing noise conditions, thereby maximizing blood pressure detection accuracy for the particular noise conditions encountered.

Further objects, features, and advantages of the invention will be apparent from the following detailed description of the invention, taken in conjunction with the accompanying drawings.

DETAILED DESCRIPTION OF THE INVENTION

Figure 1:
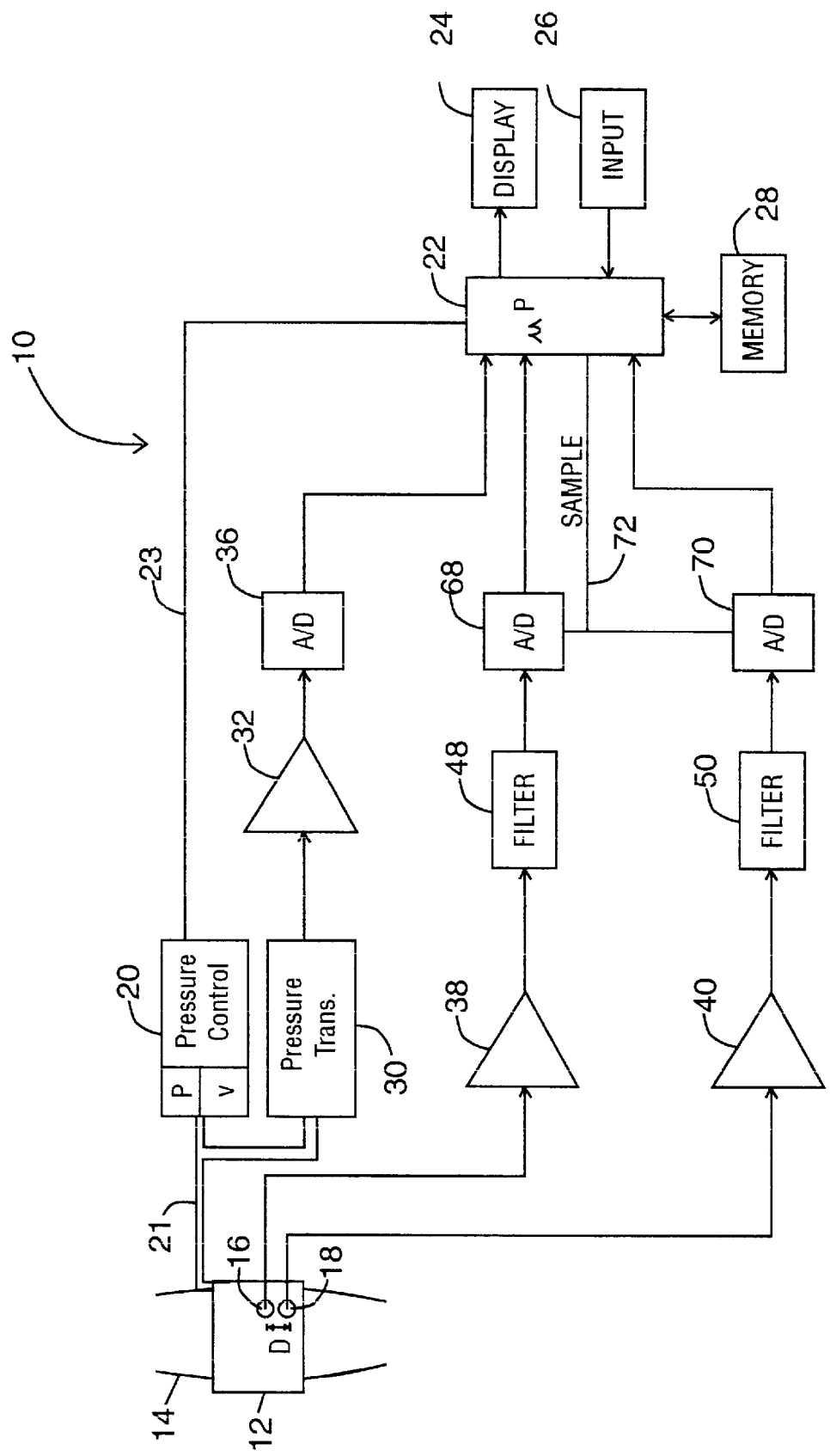
FIG. 1 is a schematic block diagram of a blood pressure monitoring system in accordance with the present invention.

A schematic block diagram of an automatic blood pressure monitoring system 10 employing the present invention is presented in FIG. 1. It should be understood that the present invention may be employed in other automatic blood pressure monitoring system topologies as well. Blood pressure monitoring system 10 preferably includes an inflatable cuff 12 that is adapted to be wrapped around the arm 14 or other appendage of a patient whose blood pressure is to be monitored. By inflating the cuff 12, pressure is applied to a brachial artery in the arm 14 of the patient, forcing the artery closed during at least part of the patient's heartbeat cycle. When the pressure in the cuff 12 is increased above the systolic blood pressure of the patient, the brachial artery in the arm 14 will become closed off entirely. The arterial wall acts in a non-linear fashion with respect to the blood pressure level. Thus, as the pressure in the cuff 14 is gradually released to below the systolic blood pressure level, but above the diastolic blood pressure level, the brachial artery will literally "snap" open following each beat of the patient's heart. This produces low frequency blood pressure sounds that are picked up by microphones 16 and 18 placed on the arm 14 of the patient beneath the cuff 12. Korotkoff sounds, produced primarily by the turbulent flow of blood through the artery following the opening of the artery, and oscillometrics may also be picked up by the microphones 16 and 18. It should be noted that the present invention is focused on the detection of the low frequency sounds produced by the opening snap of the artery, rather than blood flow sounds or oscillometrics. Generally, oscillometrics are <10 Hz and conventional auscultatory blood pressure monitoring methods use signals >50 Hz. The present invention preferably uses the low frequency blood pressure sounds in the range of approximately 15–45 Hz. It is in this sense that the term "blood pressure sounds" is used throughout this description. The microphones 16 and 18, which are preferably fixed in the cuff 12, are placed on the arm 14 of the patient near the center of the cuff 12, and along the axis of the brachial artery. The centers of the microphones are separated by a distance D such that blood pressure sounds are picked up by each microphone approximately 180°, but at least more than 90°, out of phase. When the pressure in the cuff 12 is reduced below the diastolic blood pressure level, the brachial artery will remain open between heartbeats, and the blood pressure sounds produced by the opening of the artery will disappear.

Although the cuff 12 may be manually inflated and deflated, the pressure in the cuff 12 is preferably controlled automatically by a pressure controller 20. The pressure controller 20 is connected to the cuff 12 by a tube 21 (or tubes, or a single tube with multiple lumens), and may be of a conventional design used in commercially available automatic blood pressure monitoring systems. The pressure controller 20 may, for example, include a conventional pump P for inflating the cuff 12, and one or more conventional valves V for releasing pressure from the cuff 12. The pressure controller 20 is preferably capable of inflating the cuff 12 to a cuff pressure exceeding the systolic blood pressure level of a patient, and of slowly reducing the cuff pressure from this high level to a low pressure level below the diastolic blood pressure level of the patient, either continuously or in step-wise fashion. The pressure controller may also, or alternatively, be used to gradually increase the cuff pressure from a low level, below the diastolic pressure level, to a high level, above the systolic pressure level.

The pressure controller 20 is preferably operated to inflate and deflate the cuff 12 under control of a system digital microprocessor 22 that provides control signals to the pressure controller on a line (or bus) 23. As described in more detail below, the system microprocessor 22 may be used to control the pressure controller 20 to implement a blood pressure monitoring cycle, to multiply the signals provided by the microphones 16 and 18 together to form a microphone signal product, to process the microphone signal product in blood pressure sound detection and noise signal threshold level data streams, to wave width filter the data streams, to compare the wave width filtered blood pressure sound detection data stream to a noise signal threshold level to indicate the detection of a blood pressure sound, to determine a patient's systolic and diastolic blood pressure levels based on the detected blood pressure sounds and corresponding cuff pressure levels, and to use the wave width filtered noise signal threshold level data stream to adjust the noise signal threshold level in response to changing noise conditions. A user display 24, such as a monitor, printer, LED display, or any other conventional display system, is preferably connected to the microprocessor 22 for the display of the patient's blood pressure levels and other information required by a user. The microprocessor 22 preferably also is connected to a user input 26. The user input 26 may include a keyboard, switch, push button, or other input mechanism, whereby, for example, a blood pressure monitoring cycle may be initiated, and/or operator or patient information may be entered into the system. The microprocessor 22 also preferably includes an associated memory 28, e.g., RAM, which may be implemented as a separate memory unit 28, as shown, or as an integral part of the microprocessor 22. The memory 28 is used in a conventional manner by the microprocessor for the storage of, for example, blood pressure sound and noise signal information from the microphones 16 and 18, corresponding cuff pressures, and operator or patient information input by the user through the user input 26.

The pressure in the cuff 12 at any point in time may preferably be determined using a pressure transducer 30 which may be mounted in the cuff 12, in the tube 21 connecting the cuff 12 to the pressure controller 20, or in the pressure controller 20 itself. The pressure transducer output may be filtered to reduce unwanted noise, and is applied to an amplifier 32. A conventional amplifier circuit may be used to amplify the pressure transducer signal. The amplified analog pressure signal is preferably converted to a digital signal by an analog-to-digital converter 36. Note that the analog-to-digital converter 36 may be implemented as a separate circuit component, as illustrated in FIG. 1, or may be an integral part of the microprocessor 22. The digital pressure signal from the analog-to-digital converter 36 is provided to the microprocessor 22 which may store the pressure signal value in memory 28 for later use in determining the patient's systolic and diastolic blood pressure levels. Using the pressure signal received from the analog-to-digital converter 36, the microprocessor 22 is also able to provide control signals to the pressure controller 20 on the line 23 to cause the pressure controller 20 to increase or decrease the pressure in the cuff 12 to a desired level.

Microphones 16 and 18 may be implemented in a conventional manner using commercially available microphones, sound pick-ups, transducers, etc. Sound signals picked up by the microphones 16 and 18 are amplified by microphone amplifiers 38 and 40, respectively. Conventional microphone amplifier circuits may be used to implement the microphone amplifiers 38 and 40.

The two microphones 16 and 18 may preferably be implemented using a single phase sensitive microphone assembly. In this system, two microphones are mounted on a single piece of stiff material or substrate such that the microphones act like a single microphone to noise artifacts and a differential microphone system to blood pressure sounds. The microphone system is isolated as much as possible from the cuff 12 and the environment by attaching the microphone system to the cuff 12 using a soft or padded material. This microphone system operates to keep the blood pressure sounds which are picked up by the microphones 16 and 18 out of phase, while minimizing the amount of noise picked up by the microphones 16 and 18, and keeping the noise which is picked up by the microphones 16 and 18 in phase.

The sound signal of interest to be detected by the microphones 16 and 18 is the low frequency blood pressure sound produced by the snapping open of the brachial artery. This sound has a characteristic frequency component in a known frequency band. Sound signal components picked up by the microphones 16 and 18 that are outside of this band are, therefore, probably noise. The detected and amplified microphone signals may thus be filtered by band pass filters 48 and 50 to select the frequencies corresponding to the signals of interest and to reject other frequencies which are characteristic only of noise. The desired band width for blood pressure sounds is in the range of approximately 15 Hz to 45 Hz, with a center frequency of about 30 Hz. Other band widths may also be used in accordance with the present invention. However, the low frequency blood pressure sounds produced by the snapping open of the brachial artery are generally characterized by frequencies limited to the 10 Hz to 100 Hz frequency range. The band pass filters 48 and 50 may be implemented in a conventional manner, using known band pass filter circuit topologies.

Processing of the microphone signals to reduce the noise component therein need not, however, be limited to conventional band pass filtering. For example, filtering out low frequency noise from the microphone signals is more critical than filtering out high frequency components from the microphone signals. Thus, the filters 48 and 50 are implemented as band pass filters. In general, for purposes of the present invention, the terms "filtering" and "filter" should be understood to encompass any method or apparatus for selecting a portion of the microphone signal having characteristics of blood pressure sounds and rejecting portions of the microphone signal characteristic of noise. These characteristics may be, but need not be, frequency components of the microphone signals.

Figure 2:
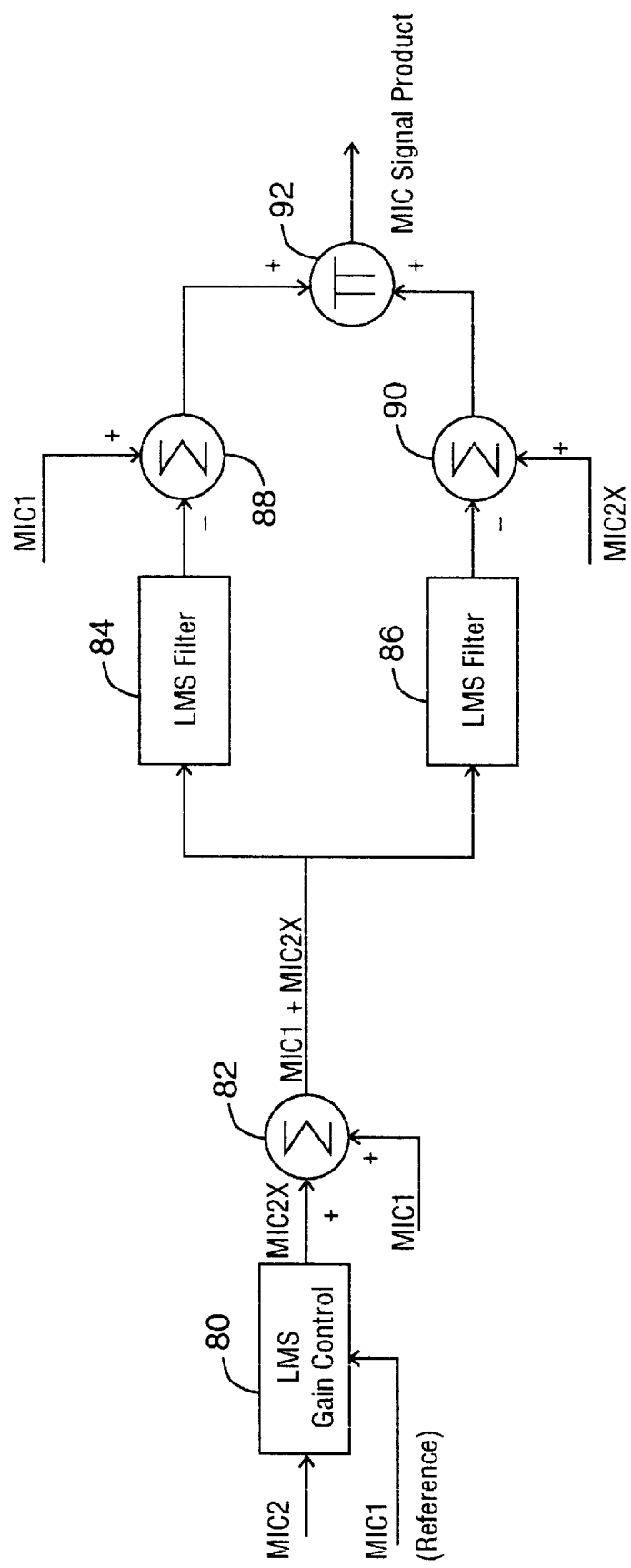
FIG. 2 is a schematic block diagram of a scheme for filtering a noise component from two microphone signals.

An exemplary alternative method for reducing the noise component in the microphone signals will be described with reference to the schematic block diagram of FIG. 2. First, one of the microphone signals (MIC2) is gain controlled so that the average value of the gain controlled microphone signal (MIC2X) matches the other microphone signal (MIC1). The gain control function may be performed using a least means square (LMS) gain control scheme 80. The gain controlled microphone signal (MIC2X) may now be added 82 to the other microphone signal (MIC1). Since the blood pressure sound components of the two microphone signals are at least 90° out of phase with each other, adding the microphone signals will tend to remove the blood pressure sound component from the combined signal, resulting in a combined signal representing mainly the noise in the microphone signals. This noise signal may be passed through LMS filters 84 and 86, such as 16 tap Widrow-Hoff filters, and then subtracted 88 and 90 from the microphone signals MIC 1 and MIC2X. It should be apparent that the effect of the subtractions 88 and 90 is to remove a noise component from the microphone signals, effectively filtering the microphone signals. The resulting processed (filtered) microphone signals may be multiplied together 92 to form a microphone signal product, which, as will be described in more detail below, is used for blood pressure monitoring with improved noise rejection in accordance with the present invention.

The method for reducing the noise component in the microphone signals described with reference to FIG. 2 may be implemented using analog circuitry, a combination of analog and digital circuits, or, preferably, may be implemented entirely in software in the system processor 22 or another digital signal processor (DSP). An exemplary computer program for implementing the filtering process described with reference to FIG. 2 follows:

```
//..................................
    sn1 = mic1_data[t] + mic1_noise[t];
    sn2 = mic2_data[t] + mic2_noise[t];
//.... Auto LMS Gain Control.....................
    sn2g = (float) sn2 * gain;
    diff = abs(sn1) - abs (sn2g);
    gain += (float) diff * abs(sn2) * 0.00000001;
//.... Widrow - Hoff LMS Filter..................
    for(inz=TAPS-1; inz>0; --inz)
        data_buffer1[inz] = data_buffer1[inz-1];
    data_buffer1[0] = sn1 + sn2g;
    for(inz=0, accum1=0.0; inz<TAPS; ++inz)
        accum1 += data_buffer1[inz] * wt_buffer1[inz];
    output1 = sn1 - accum1;
    for (inz=0; inz<TAPS; ++inz)
        wt_buffer1[inz] += 0.000000002 * output1 *
            data_buffer1[inz];
    for (inz=TAPS-1; inz>o; --inz)
        data_buffer2[inz] = data_buffer2[inz-1];
    data_buffer2[0] = sn1 + sn2g;
    for(inz=0; accum2=0.0; inz<TAPS; ++inz)
        accum2 += data_buffer2[inz] * wt_buffer2[inz];
    output2 = sn2g - accum2;
    for(inz=0; inz<TAPS; ++inz)
        wt_buffer2[inz] += 0.000000002 * output2 *
            data_buffer2[inz];
//.... Cross Correlation........................
    bpsure_out = output1 * output2;
//.....................................
```

Where more conventional band pass filtering is used, the outputs of the filters 48 and 50 may be analog signals which preferably are converted to digital signals by analog-to-digital converters 68 and 70, respectively. Note that the analog-to-digital converters 68 and 70 may be implemented as separate components, as illustrated, or may be integral parts of the system microprocessor 22. The outputs of the analog-to-digital converters 68 and 70, corresponding to digitized filtered signals from microphones 16 and 18, are provided to the microprocessor 22, which employs the digital signals to detect blood pressure sounds in the presence of significant noise in the manner to be described in more detail below.

In accordance with the present invention, blood pressure sounds produced by the snapping open of the brachial artery are detected based upon information contained in the signals from the two microphones 16 and 18. Since the present invention does not employ time gating, it does not matter which microphone 16 or 18 is placed upstream of the other. However, both microphones 16 and 18 are preferably placed along the axis of the brachial artery. The centers of the two microphones 16 and 18 preferably are separated by the distance D such that a blood pressure sound will be picked up approximately 180°, but at least more than 90°, out of phase by each microphone. The low frequency blood pressure sound produced by the snapping open of the brachial artery represents a relatively slow pulse wave when compared with the speed of sound at which most noise signals will travel. Thus, for two microphones 16 and 18 having centers separated by a distance D, whereas the signal of interest, the blood pressure sound signal, will be out of phase for each microphone 16 and 18, a noise signal will be picked up essentially simultaneously and in phase by each microphone 16 and 18.

As discussed previously, the frequency range of interest for blood pressure sounds is approximately 15 Hz to 45 Hz, with a center frequency of about 30 Hz. At 30 Hz, the time required to complete one cycle is 33 milliseconds. To produce the maximum phase shift between the two microphone signals, therefore, the centers of the two microphones 16 and 18 should be separated by a distance D that produces a delay in the detected blood pressure sound pulse equivalent to one-half of a cycle, i.e., 17 milliseconds. It is known that the pulse wave produced by the blood pressure sound propagates down the arm 14 at approximately 1–2 meters per second. Thus, centering the microphones 16 and 18 approximately D=2.5 centimeters apart provides the desired delay between the signals from each microphone 16 and 18. The microphones 16 and 18 may be fixed in the cuff at this separation distance. Analysis of signals obtained during tests on human subjects reveal maximum phase shifts when these parameters are used. It should be noted that a slightly larger or smaller distance D between the centers of the two microphones 16 and 18 may be used without dramatically affecting the ability of the present invention to detect blood pressure sounds in the presence of significant noise. The separation distance D should, however, be such that blood pressure sounds picked up by the microphones 16 and 18 are at least 90° out of phase.

In accordance with the present invention, a wave width filtered blood pressure sound detection signal is extracted from the product of the two microphone signals. The wave width filtered blood pressure sound detection signal is compared to a noise signal threshold level to determine whether the wave width filtered blood pressure sound detection signal represents the detection of a blood pressure sound. If a blood pressure sound detection is indicated, this information, along with the cuff pressure, may be used to determine the systolic and diastolic blood pressure levels of a patient. A wave width filtered noise amplitude signal may also be extracted from the microphone signal product, and used to adjust the noise signal threshold level in response to changing noise conditions.

To extract the desired information from the two microphone signals, the two amplified and filtered microphone signals are preferably sampled at a relatively high rate, e.g., 500 Hz–2,000 Hz. This may be accomplished, for example, by a SAMPLE signal applied at the desired frequency to the analog-to-digital converters 68 and 70 from the microprocessor 22 on a line 72. This SAMPLE signal causes the digital signals corresponding to the filtered microphone signals to be provided to the microprocessor 22 at the desired sampling rate. Of course, the sampling may be accomplished entirely internal to the microprocessor 22, particularly where the analog-to-digital converters 68 and 70 are implemented as integral parts of the microprocessor 22.

Figure 3:
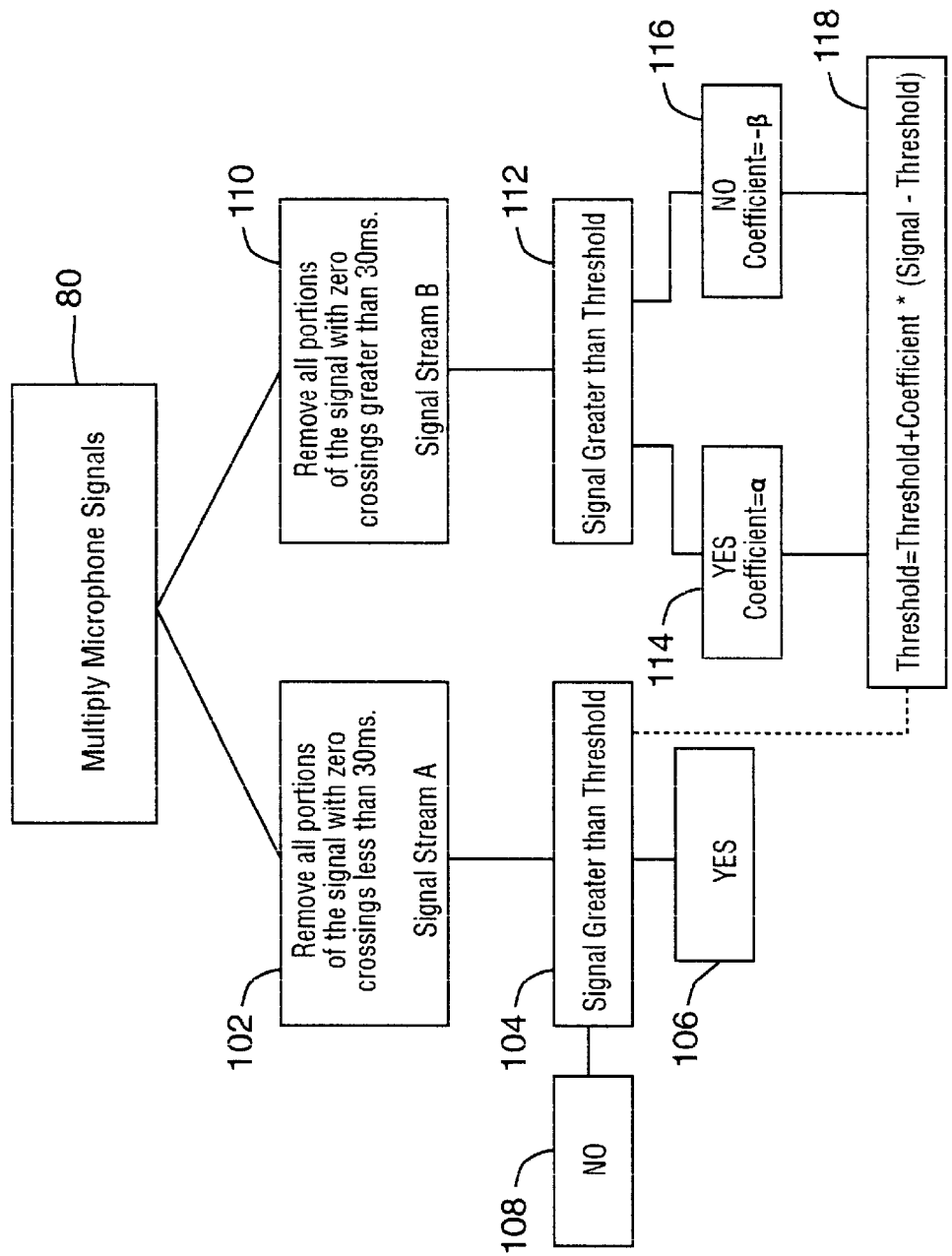
FIG. 3 is a flow chart diagram illustrating the steps of a method in accordance with the present invention for detecting blood pressure sounds in the presence of noise and for adjusting a noise signal threshold level in response to changing noise conditions.

The operational steps which are implemented by the system microprocessor 22 to process the two sampled microphone signals in accordance with the present invention, to determine therefrom whether a blood pressure sound is detected, are described with reference to the flow chart diagram of FIG. 3. The operational steps to be described may be implemented in the system microprocessor 22 using conventional programming techniques well-known to those skilled in the art of microprocessor system programming.

Processing of the microphone signals begins at step 100, where the two sampled microphone signals are multiplied together. At each sample time, a value for the state (amplitude and sign) of each of the microphone signals is provided. The two microphone signal sample values are multiplied together at step 100 to generate a microphone signal product. This multiplication may be accomplished directly, in the time domain, or may be achieved by transforming the sampled microphone signals into the frequency domain and then convolving the two transformed signals. In accordance with the present invention, the microphone signal product is processed along two separate data streams, a blood pressure sound detection signal data stream (designated signal stream A in FIG. 3), and a noise signal threshold level data stream (designated signal stream B in FIG. 3). Processing in the two data streams preferably occurs effectively in parallel. Processing of the microphone signal product in the blood pressure sound detection signal data stream (stream A) is performed to determine the detection of a blood pressure sound, and will be described in detail first. Processing of the microphone signal product in the noise signal threshold level data stream (stream B) is performed to adjust a noise signal threshold level in response to changing noise conditions, and will be described in more detail below.

At step 102, a wave width filter function is applied to the microphone signal product to remove all portions of the microphone signal product whose wave width is less than a selected minimum wave width value. Thus, only those portions of the microphone signal product having a wave width, from zero crossing to zero crossing, that is greater than the selected minimum wave width value will be passed through step 102. The selected wave width value is selected such that the wave width filtered blood pressure sound detection signal provided by step 102 will include all portions of the microphone signal product which correspond to blood pressure sounds, with some of the portions of the microphone signal product which correspond to noise removed. An exemplary and preferred selected minimum wave width value is 30 ms. Blood pressure sounds will produce a microphone signal product wave width greater than this selected minimum wave width value. Noise appearing in the microphone signal product will have wave widths both longer and shorter than this same minimum wave width value. Thus, the wave width filtered blood pressure sound detection signal will include all of the data from the microphone signal product which corresponds to blood pressure sounds, with some of the noise from the microphone signal product removed.

The wave width filter function of step 102 may be implemented in the system microprocessor 22 using conventional programming techniques. A preferred routine for implementing the wave width filtering function of step 102 is as follows. Each time the microphone signals are sampled and multiplied together at step 100 a microphone signal product value is produced. This microphone signal product value will be positive or negative in sign, and will have a microphone signal product amplitude value. A counter is incremented at each sample instant as long as the microphone signal product maintains the same sign. Also, at each sample time, the microphone signal product amplitude value is compared with a previously stored microphone signal product amplitude value. If the new microphone signal product amplitude value is greater than the previously stored microphone signal product amplitude value, the new microphone signal product amplitude value is stored. In this way, the maximum amplitude of the microphone signal product between zero crossings of the microphone signal product is maintained. When the sign of the microphone signal product changes, indicating a zero crossing of the microphone signal product, the value stored in the counter is examined. If the counter value indicates that less than the selected minimum wave width time (e.g., 30 ms) has elapsed since the last zero crossing of the microphone signal product, the stored maximum microphone signal product amplitude value is zeroed out. If the counter value indicates that more than the selected minimum wave width time has elapsed since the last zero crossing of the microphone signal product, the stored maximum microphone signal product amplitude value is provided to the next step in the blood pressure sound detection signal data stream process. It is apparent that this routine provides the maximum amplitude of portions of the microphone signal product whose wave width is longer than the selected minimum wave width value to the next processing step. For portions of the microphone signal product whose wave width is less than the minimum wave width value, the wave width filtering routine provides a zero output. After the microphone signal product changes signs, e.g., goes from positive to negative, both the counter and the stored maximum microphone signal product amplitude value are reinitialized to zero. The routine is then repeated, the counter is incremented at each sampling instant and the maximum microphone signal product amplitude value is maintained, until the next zero crossing of the microphone signal product is detected (e.g., when the microphone signal product goes from negative to positive). Note that zero crossings preferably may be detected by the microphone signal product exceeding or dropping below a selected small positive or negative signal value. Thus, the wave width may preferably be determined approximately between zero crossings.

At step 104, the output of the wave width filtered blood pressure sound detection signal provided by step 102 is compared to a noise signal threshold level. If the wave width filtered blood pressure sound detection signal is greater than the noise signal threshold level, a blood pressure sound detection is indicated at step 106. If the wave width filtered blood pressure sound detection signal does not exceed the noise signal threshold level, the signal is assumed to be noise, rather than a blood pressure sound detection, as indicated at step 108. Note that the noise signal threshold level is always greater than or equal to zero. Therefore, if the output of the wave width filtering function of step 102 is zero, indicating a portion of the microphone signal product whose wave width is too short to constitute a blood pressure sound, the result of the comparison made in step 104 will always be an indication that this portion of the microphone signal product is noise.

The noise signal threshold level is dynamically adjusted in response to changing noise conditions based on the microphone signal product as processed in the noise signal threshold level data stream. Processing of the microphone signal product in the noise signal threshold level data stream will now be described. At step 110, a wave width filter function is applied to the microphone signal product in the noise signal threshold level data stream (signal stream B). This wave width filtering function 110 removes all portions of the microphone signal product whose wave width, from zero crossing to zero crossing, is greater than a selected maximum wave width value. Only those portions of the microphone signal product having wave widths shorter than the selected maximum wave width value are passed through step 110 to the next processing step in the noise signal threshold level data stream. For portions of the microphone signal product having wave widths greater than the selected maximum wave width value, the output of step 110 is zero. The maximum wave width value is selected such that the output of the wave width filter function 110 is a wave width filtered noise amplitude signal which represents only noise content of the microphone signals. The output of the wave width filter function 110 should contain no blood pressure sound information. Thus, the maximum wave width value is selected to be less than the microphone signal product wave width produced by a blood pressure sound. Since blood pressure sounds will produce microphone signal product wave widths longer than the selected maximum wave width, all blood pressure sound information will be removed from the microphone signal product by the wave width filter function of step 110. Since noise picked up by the microphones 16 and 18 may have a microphone signal product wave width which is either longer or shorter than the selected maximum wave width, the output of the wave width filter 110 will contain only noise portions of the microphone signal product. The wave width filtered noise amplitude signal provided by wave width filtering function 110 is thus representative of the noise conditions being experienced by the blood pressure monitoring system 10. Preferably, the maximum wave width value may be selected to be the same as the selected minimum wave width value used in the wave width filtering function 102 in the blood pressure sound detection signal data stream (e.g., 30 ms).

The wave width filter function of step 110 may be implemented in the system microprocessor 22 using conventional programming techniques. A preferred routine for implementing the wave width filtering function of step 110 is as follows. Each time the microphone signals are sampled and multiplied together at step 100 a microphone signal product having a positive or negative sign and a microphone signal product amplitude value is produced. A counter value initially is incremented at each sampling instant as long as the microphone signal product maintains the same sign. Also, at each sample time, the microphone signal product amplitude value is compared with a previously stored microphone signal product amplitude value. If the new microphone signal product amplitude value exceeds the previously stored microphone signal product amplitude value, the new microphone signal product amplitude value is stored in place of the previously stored microphone signal product amplitude value. In this way, the routine keeps track of the maximum amplitude of the microphone signal product between zero crossings of the microphone signal product. Incrementing the counter with each new sample, and maintaining the maximum amplitude of the microphone signal product, is continued until either the microphone signal product value changes sign (e.g., goes from positive to negative), or the counter value exceeds a threshold value, indicating that the current wave width is wider than the selected maximum wave width value. At each new sample instant, after incrementing the counter, the counter value is compared to a threshold value related to the selected maximum wave width value. If the counter value exceeds the threshold value, indicating that the time elapsed since the last zero crossing of the microphone signal product is greater than the selected maximum wave width value, the stored maximum microphone signal product amplitude value is set to zero. This value is maintained at zero until a zero crossing of the microphone signal product is indicated by a change in sign of the microphone signal product value. When a zero crossing of the microphone signal product is detected, by a change in sign of the microphone signal product from positive to negative or negative to positive, the stored maximum microphone signal product amplitude value is provided as the output of step 110 to the next step in the noise signal threshold level data stream process. If the width of the current microphone signal product wave pulse, from zero crossing to zero crossing, was greater than the selected maximum wave width value, the output value provided by the wave width filter function 110 will be zero. Otherwise, the output value provided by the wave width filter function 110 will be the maximum amplitude of the microphone signal product since the last zero crossing of the microphone signal product. Following the detection of a zero crossing of the microphone signal product, the counter value and the stored maximum microphone signal product amplitude value are both reinitialized to zero. The procedure of incrementing the counter and comparing the counter value to a threshold value at each sample time, and maintaining the maximum amplitude of the microphone signal product, is then repeated until another zero crossing of the microphone signal product is detected. Note that, as described previously, zero crossings preferably may be detected by the microphone signal product exceeding or dropping below a selected small positive or negative signal value. Thus, the wave width may actually be determined approximately between zero crossings.

The wave width filtered noise amplitude signal output of the wave width filter function of step 110 is compared to the noise signal threshold level at step 112. If the wave width filtered noise amplitude signal is greater than the noise signal threshold level, an increasing noise condition is indicated. In such a case, a noise signal threshold level adjustment coefficient is set to a selected value a at step 114. If the wave width filtered noise amplitude signal output of step 110 is less than the noise signal threshold level, a decreasing noise condition is indicated. In such a case, the noise signal threshold level adjustment coefficient is set to a selected value -$\beta$ at step 116. At step 118, the noise signal threshold level is adjusted in response to the changing noise condition. A new noise signal threshold level is established as the current noise signal threshold level plus the product of the noise signal threshold level adjustment coefficient and the difference between the wave width filtered noise amplitude signal and the current noise signal threshold level. The adjusted noise signal threshold level provided by step 118 is used in step 104 in the blood pressure sound detection signal processing stream to determine if the microphone signal product indicates a blood pressure sound detection, as described previously. Note that steps 114–118 preferably are executed only when the value provided by the wave width filter function step 110 is non-zero.

The first noise signal threshold level adjustment coefficient value $\alpha$, used to increase the noise signal threshold level in response to increasing noise conditions, is preferably much larger than the second noise signal threshold level adjustment coefficient value $\beta$, used to reduce the noise signal threshold level in response to decreasing noise conditions. Thus, the noise signal threshold level will be increased rapidly in response to increasing noise conditions, but will be decreased only gradually in response to decreasing noise conditions. This conservative approach prevents the noise signal threshold level from being reduced too quickly in response to only transient or temporary noise reductions in an otherwise highly noisy environment. Dynamic adjustment of the noise signal threshold level in changing noise environments minimizes false positive blood pressure sound detections in noisy environments while minimizing false negative blood pressure sound detections (missed detections) in less noisy environments. This enhances the overall reliability and accuracy of a blood pressure monitoring system 10 employing improved noise rejection in accordance with the present invention.

The computations performed in the blood pressure sound detection signal data stream (signal stream A) may be performed with a constant delay. Thus, the output of the blood pressure sound detection signal data stream may be delayed from the signal input to the blood pressure sound detection signal data stream. Similarly, the computation of a new noise signal threshold level in the noise signal threshold level data stream (signal stream B) may be delayed from the signal input to the noise signal threshold level data stream. Preferably, the delay in the noise signal threshold level data stream is less than the delay in the blood pressure sound detection signal data stream. Hence, the noise signal threshold level is preferably adjusted based on signal data which precedes in time the signal data used to determine the detection of a blood pressure sound in the blood pressure sound detection signal data stream. In effect, when wave width filtered signal data is compared at step 104 to the noise signal threshold level, the comparison is made based on noise signal data from the future. The noise rejection capability of the system is thereby improved, in that the noise signal threshold level may be adjusted in response to a noise burst before a blood pressure sound detection determination is made during that same noise burst.

Figure 4:
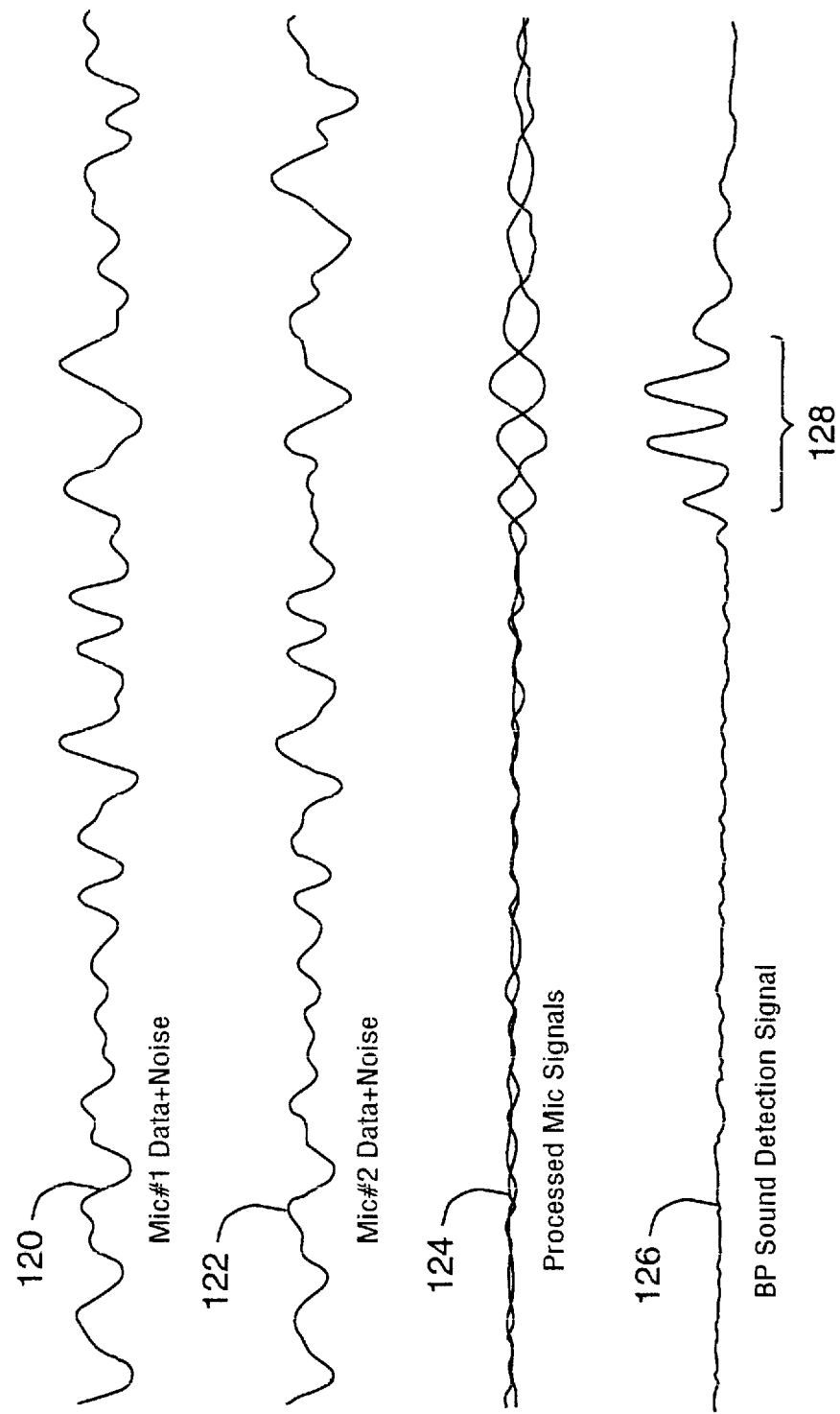
FIGS. 4 and 5 are waveform diagrams of two exemplary microphone signals produced by a blood pressure monitoring system in accordance with the present invention, the microphone signals after being processed to filter a noise component therefrom, and the signal resulting from an improved noise rejection method in accordance with the present invention applied to the processed microphone signals.

The operation of a blood pressure monitoring system employing improved noise rejection in accordance with the present invention to distinguish blood pressure sound detections from noise is further described with reference to the exemplary waveforms presented in FIG. 4. FIG. 4 illustrates exemplary microphone signal waveforms 120 and 122, such as may be produced by microphones 16 and 18 of exemplary blood pressure monitoring system 10. Waveform 124 is the microphone signals 120 and 122 after they have been filter processed to remove noise therefrom. Waveform 126 is the processed microphone signal product, wherein a heartbeat 128 is clearly distinguishable.

During the heartbeat 128, the product of the two microphone signals 120 and 122 is a microphone signal product 126 wave pulse having a wave width which exceeds the selected minimum wave width value, e.g., 30 milliseconds, and having an amplitude which exceeds the noise signal threshold level. Thus, during the heart beat 128, a blood pressure sound detection system employing improved noise rejection in accordance with the present invention will indicate the detection of a blood pressure sound, corresponding to the occurrence of a heartbeat cycle.

Systolic and diastolic blood pressure levels of a patient may be determined based on the blood pressure sounds that are detected in accordance with the present invention as previously described. This may be accomplished in a usual manner employed for automatic auscultatory blood pressure determinations. An exemplary automated procedure for determining the systolic and diastolic blood pressure levels of a patient using the blood pressure monitoring system 10 shown in FIG. 1 employing the method for detecting blood pressure sounds of the present invention is as follows.

The inflatable cuff 12 is placed around the arm 14 of a patient with the two microphones 16 and 18 fixed therein placed against the arm 14 of the patient near the center of the cuff and along the axis of a brachial artery. The centers of the microphones 16 and 18 are separated by the distance D, e.g., 2.5 centimeters, such that a blood pressure sound picked up by the two microphones 16 and 18 will be approximately 180°, but at least more than 90°, out of phase. A user may initiate a blood pressure monitoring cycle through, for example, the user input 26 to the microprocessor 22. Microprocessor 22 then provides control signals on the line 23 to the pressure controller 20 which will increase the pressure in the cuff 12 to well above the maximum probable systolic blood pressure level of the patient to close the brachial artery in the arm 14. The microprocessor 22 then controls the pressure controller 20 to slowly reduce the pressure in the cuff 12. The pressure may be reduced at a slow continuous rate or in incremental steps. As the pressure is being slowly released from the cuff 12, the procedure in accordance with the present invention for distinguishing blood pressure sounds from noise is initiated. When the detection of a blood pressure sound is first indicated, the cuff pressure at that time, determined using the pressure transducer 30, is recorded by the microprocessor 22 in memory 28. This pressure corresponds to the systolic blood pressure level of the patient, which may be displayed to the user on the system display 24. As the pressure in the cuff 12 continues to be gradually released, blood pressure sounds will continue to be detected. Each time a blood pressure sound detection is indicated, the cuff pressure at that time is recorded in memory 28 by the microprocessor 22. If, following a blood pressure sound detection, no further blood pressure sound detections are indicated for a selected period of time, the cuff pressure at the time of the last indication of a blood pressure sound detection is recorded in memory 28 as corresponding to the diastolic blood pressure level of the patient. The diastolic blood pressure level may then be displayed to the user on the blood pressure monitor system display 24. The remaining pressure in the cuff 12 may then be released rapidly.

Figure 5:
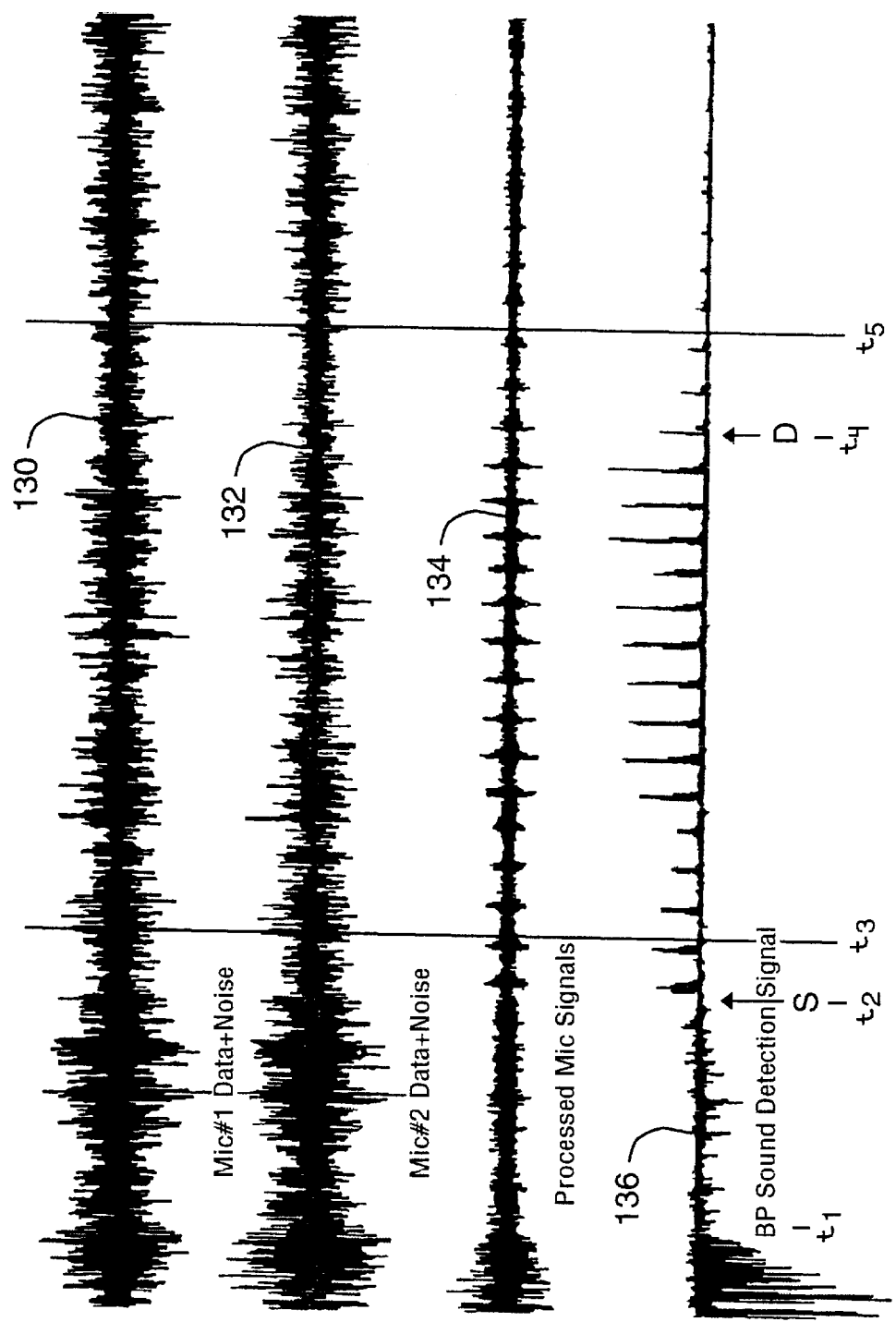

The operation of a blood pressure monitoring system employing improved noise rejection in accordance with the present invention to determine systolic and diastolic blood pressure levels of a patient is further described with reference to the exemplary waveforms presented in FIG. 5. FIG. 5 illustrates exemplary microphone signals 130 and 132, such as may be produced by microphones 16 and 18 of exemplary blood pressure monitoring system 10, over a blood pressure monitoring cycle during which cuff pressure is reduced gradually from above a systolic blood pressure level to below a diastolic blood pressure level. Waveform 134 is the microphone signals 130 and 132 after they have been filter processed by the method described with reference to FIG. 2 to remove noise therefrom. Waveform 136 is the processed microphone signal product. Note that before time $t_1$ the filters are learning and adjusting filter weights. At time $t_2$ the product of the two microphone signals 136 is a microphone signal product wave pulse having a wave width which exceeds the selected minimum wave width value and having an amplitude which exceeds the noise signal threshold level. Thus, at time $t_2$, a blood pressure sound detection is indicated. Since this is the first blood pressure sound detection made during the gradual release of cuff pressure, the cuff pressure at time $t_2$ corresponds to the systolic blood pressure level of the patient. The systolic blood pressure level may be called out (e.g., displayed) a few heartbeats later, at time $t_3$. As the cuff pressure continues to be reduced, further blood pressure sound detections are made. Following a blood pressure sound detection made at time $t_4$, no further blood pressure sound detections are made as the cuff pressure is reduced further. Thus, the cuff pressure at time $t_4$ corresponds to the diastolic blood pressure level of the patient. The diastolic blood pressure level may be called out (e.g., displayed) a few heartbeats later, at time $t_5$.

Various other blood pressure monitoring systems and methods may employ the method and apparatus of the present invention for distinguishing blood pressure sounds from noise. For example, blood pressure sound detections may be made as the pressure in the cuff is slowly increased from below the minimum probable diastolic blood pressure level to above the systolic blood pressure level of a patient. In this case, the cuff pressure at the first detection of a blood pressure sound corresponds to the diastolic blood pressure level, and the cuff pressure at which a blood pressure sound detection is last indicated corresponds to the systolic blood pressure level. The blood pressure measurement cycle may be terminated, and the pressure in the cuff released, when blood pressure sounds are no longer detected. This method may be employed to reduce the maximum pressure applied to the arm 14, since it is not necessary to estimate a high starting cuff pressure, well above the probable systolic blood pressure level of the patient, at which to initiate the blood pressure measurement cycle. Since the present invention is capable of distinguishing blood pressure sounds from noise, noise produced by the pump P will not prevent accurate blood pressure level determinations during cuff inflation.

A method or apparatus in accordance with the present invention for improving noise rejection in the detection of blood pressure sounds may be used in combination with various blood pressure monitoring devices to improve the performance of such devices in highly noisy environments. For example, improved noise rejection in accordance with the present invention may be employed in combination with the blood pressure monitoring system described in pending U.S. patent application Ser. No. 08/665,286, entitled "Method and Apparatus for Detecting Blood Pressure by Blood Pressure Sounds in the Presence of Significant Noise", filed Jun. 17, 1996, the disclosure of which is hereby incorporated by reference. This blood pressure monitoring system employs the phase information contained in two microphone signals to distinguish blood pressure sound detections from noise. The two microphones are placed on a patient along the axis of an artery with their centers separated by a distance such that blood pressure sounds picked up by the microphones will be out of phase. As pressure is applied to the artery, the two microphone signals are filtered, sampled, and multiplied together to produce a microphone signal product. If the microphone signal product is negative for more than a selected number of consecutive samples, the detection of a blood pressure sound is indicated. This method of detecting a blood pressure sound relies on the phase information contained in the microphone signal product. In accordance with the present invention, this blood pressure sound detection method may be enhanced by employing the amplitude information contained in the microphone signal product as well. Thus, in accordance with the present invention, a blood pressure monitoring system may be implemented wherein the detection of a blood pressure sound is indicated when both the microphone signal product over a selected sampling period is negative and the microphone signal product wave width over the sampling period is greater than a selected minimum wave width value and the maximum amplitude of the microphone signal product wave pulse exceeds a noise signal threshold level, as described previously. The noise signal threshold level is preferably dynamically adjusted in response to changing noise conditions, based on the microphone signal product, as described previously.

The present invention may also be employed as a stage in a blood pressure monitoring system or method in which a patient's blood pressure is determined from a plot of the delay times between an ECG signal and the detection of a blood pressure sound at the inflatable cuff 12 for various cuff pressure levels. In such a blood pressure monitoring system, the present invention would be used to detect accurately the occurrence of a blood pressure sound in the presence of significant noise. The blood pressure sound detection method and apparatus of the present invention may be employed in any blood pressure monitoring system, or other medical device requiring the accurate detection of blood pressure sounds, to improve the performance of such a device in highly noisy environments.

Although the present invention has been illustrated and described as implemented using a digital microprocessor 22, it is apparent that the present invention may be implemented using a combination of analog and/or digital components. For example, multiplication of the two filtered microphone signals may be accomplished using an analog multiplier. Conversion of the microphone signals to the frequency domain, and convolution of the resulting frequency domain spectra, may be accomplished using software or dedicated integrated circuits. Wave width filtering of the microphone signal product may be accomplished using analog devices. Signal comparisons may be accomplished using analog comparitors.

It is understood that this invention is not confined to the particular embodiments, implementations, and applications herein illustrated and described, but embraces all such modified forms thereof as come within the scope of the following claims.

What is claimed is:

1. A method for detecting a blood pressure sound in a patient, comprising the steps of:
    (a) placing a first microphone on the patient near the location of an artery, the first microphone producing a first microphone signal in response to blood pressure sounds and noise picked up by the first microphone;
    (b) placing a second microphone on the patient near the location of the artery and separated a distance from the first microphone, the second microphone producing a second microphone signal in response to blood pressure sounds and noise picked up by the second microphone;
    (c) applying pressure to the artery such that the artery will be forced closed during part of a heart beat cycle and will be forced open during part of the heart beat cycle when the patient's blood pressure exceeds the pressure applied to the artery, the opening of the artery causing a blood pressure sound to be produced;
    (d) multiplying the first and second microphone signals to generate a microphone signal product;
    (e) wave width filtering the microphone signal product to remove therefrom portions of the microphone signal product having a wave width which is less than a selected minimum wave width value to generate a wave width filtered blood pressure sound detection signal;
    (f) comparing the wave width filtered blood pressure sound detection signal to a noise signal threshold level; and
    (g) indicating the detection of a blood pressure sound when the wave width filtered blood pressure sound detection signal exceeds the noise signal threshold level.

2. The method of claim 1 wherein the second microphone is placed on the patient such that a center of the second microphone is separated a distance from a center of the first microphone such that a blood pressure sound picked up by the first microphone will be picked up out of phase by the second microphone.

3. The method of claim 1 comprising additionally the step of selecting portions of the first and second microphone signals having characteristics corresponding to blood pressure sounds before multiplying the first and second microphone signals.

4. The method of claim 3 wherein the step of selecting portions of the first and second microphone signals includes the step of filtering the first and second microphone signals with filters having pass bands corresponding approximately to the frequency range of blood pressure sounds.

5. The method of claim 3 wherein the step of selecting portions of the first and second microphone signals includes the steps of:
    (a) gain controlling one of the first and second microphone signals to match the average levels of the first and second microphone signals;
    (b) adding the microphone signals together to create a microphone signal sum in which a blood pressure sound component of the two microphone signals is reduced;
    (c) least means square filtering the microphone signal sum; and
    (d) subtracting the least means square filtered microphone signal sum from each of the first and second microphone signals.

6. The method of claim 1 wherein the selected minimum wave width value is less than a minimum wave width of a blood pressure sound.

7. The method of claim 1 wherein the step of applying pressure to the artery includes the step of inflating an inflatable cuff wrapped around an arm of the patient, and wherein the first and second microphones are placed on the arm of the patient under the inflatable cuff along an axis of the artery.

8. The method of claim 1 comprising additionally the step of adjusting the noise signal threshold level in response to changing noise conditions.

9. A method for detecting a blood pressure sound in a patient, comprising the steps of:
    (a) placing a first microphone on a patient near the location of an artery, the first microphone producing a first microphone signal in response to blood pressure sounds and noise picked up by the first microphone;
    (b) placing a second microphone on the patient near the location of the artery and separated a distance from the first microphone, the second microphone producing a second microphone signal in response to blood pressure sounds and noise picked up by the second microphone;
    (c) applying pressure to the artery such that the artery will be forced closed during part of a heart beat cycle and will be forced open during part of the heart beat cycle when the patient's blood pressure exceeds the pressure applied to the artery, the opening of the artery causing a blood pressure sound to be produced;
    (d) multiplying the first and second microphone signals to generate a microphone signal product;
    (e) wave width filtering the microphone signal product to remove therefrom portions of the microphone signal product having a wave width which is less than a selected minimum wave width value to generate a wave width filtered blood pressure sound detection signal;
    (f) comparing the wave width filtered blood pressure sound detection signal to a noise signal threshold level;
    (g) indicating the detection of a blood pressure sound when the wave width filtered blood pressure sound detection signal exceeds the noise signal threshold level;
    (h) wave width filtering the microphone signal product to remove therefrom portions of the microphone signal product having a wave width which is greater than a selected maximum wave width value to generate a wave width filtered noise amplitude signal;
    (i) comparing the wave width filtered noise amplitude signal to the noise signal threshold level;
    (j) increasing the noise signal threshold level by an amount related to the product of a first noise signal threshold level adjustment coefficient and a difference between the noise signal threshold level and the wave width filtered noise amplitude signal if the wave width filtered noise amplitude signal exceeds the noise signal threshold level; and (k) decreasing the noise signal threshold level by an amount related to the product of a second noise signal threshold level adjustment coefficient and the difference between the noise signal threshold level and the wave width filtered noise amplitude signal if the wave width filtered noise amplitude signal is less than the noise signal threshold level.

10. The method of claim 9 wherein the second microphone is placed on the patient such that a center of the second microphone is separated a distance from a center of the first microphone such that a blood pressure sound picked up by the first microphone will be picked up out of phase by the second microphone.

11. The method of claim 9 comprising additionally the step of selecting portions of the first and second microphone signals having characteristics corresponding to blood pressure sounds before multiplying the first and second microphone signals.

12. The method of claim 11 wherein the step of selecting portions of the first and second microphone signals includes the step of filtering the first and second microphone signals with filters having pass bands corresponding approximately to the frequency range of blood pressure sounds.

13. The method of claim 1 wherein the step of selecting portions of the first and second microphone signals includes the steps of:

(a) gain controlling one of the first and second microphone signals to match the average levels of the first and second microphone signals;

(b) adding the microphone signals together to create a microphone signal sum in which a blood pressure sound component of the two microphone signals is reduced;

(c) least means square filtering the microphone signal sum; and (d) subtracting the least means square filtered microphone signal sum from each of the first and second microphone signals.

14. The method of claim 9 wherein the selected minimum wave width value is less than a minimum wave width of a blood pressure sound.

15. The method of claim 9 wherein the selected maximum wave width value is less than a minimum wave width of a blood pressure sound.

16. The method of claim 9 wherein the selected minimum wave width value and the selected maximum wave width value are equal.

17. The method of claim 9 wherein the first noise signal threshold level adjustment coefficient is larger than the second noise signal threshold level adjustment coefficient.

18. The method of claim 9 wherein the step of applying pressure to the artery includes the step of inflating an inflatable cuff wrapped around an arm of the patient, and wherein the first and second microphones are placed on the arm of the patient under the inflatable cuff along an axis of the artery.

19. The method of claim 9 wherein the step of comparing the wave width filtered blood pressure sound detection signal to the noise signal threshold level is delayed from the steps of increasing or decreasing the noise signal threshold level such that the wave width filtered blood pressure sound detection signal based on the microphone signal product is compared to a noise signal threshold level which is increased or decreased based on a microphone signal product from a future point in time.

20. A method for adjusting a noise signal threshold level in response to changing noise conditions during the detection of blood pressure sounds in a patient, comprising the steps of:

(a) placing a first microphone on a patient near the location of an artery, the first microphone producing a first microphone signal in response to blood pressure sounds and noise picked up by the first microphone;

(b) placing a second microphone on the patient near the location of the artery and separated a distance from the first microphone, the second microphone producing a second microphone signal in response to blood pressure sounds and noise picked up by the second microphone;

(c) applying pressure to the artery such that the artery will be forced closed during part of a heart beat cycle and will be forced open during part of the heart beat cycle when the patient's blood pressure exceeds the pressure applied to the artery, the opening of the artery causing a blood pressure sound to be produced;

(d) multiplying the first and second microphone signals to generate a microphone signal product;

(e) wave width filtering the microphone signal product to remove therefrom portions of the microphone signal product having a wave width which is greater than a selected maximum wave width value to generate a wave width filtered noise amplitude signal;

(f) comparing the wave width filtered noise amplitude signal to the noise signal threshold level;

(g) increasing the noise signal threshold level by an amount related to the product of a first noise signal threshold level adjustment coefficient and a difference between the noise signal threshold level and the wave width filtered noise amplitude signal if the wave width filtered noise amplitude signal exceeds the noise signal threshold level; and (h) decreasing the noise signal threshold level by an amount related to the product of a second noise signal threshold level adjustment coefficient and the difference between the noise signal threshold level and the wave width filtered noise amplitude signal if the wave width filtered noise amplitude signal is less than the noise signal threshold level.

21. The method of claim 20 wherein the second microphone is placed on the patient such that a center of the second microphone is separated a distance from a center of the first microphone such that a blood pressure sound picked up by the first microphone will be picked up out of phase by the second microphone.

22. The method of claim 20 comprising additionally the step of selecting portions of the first and second microphone signals having characteristics corresponding to blood pressure sounds before multiplying the first and second microphone signals.

23. The method of claim 22 wherein the step of selecting portions of the first and second microphone signals includes the step of filtering the first and second microphone signals with filters having pass bands corresponding approximately to the frequency range of blood pressure sounds.

24. The method of claim 22 wherein the step of selecting portions of the first and second microphone signals includes the steps of:

(a) gain controlling one of the first and second microphone signals to match the average levels of the first and second microphone signals;

(b) adding the microphone signals together to create a microphone signal sum in which a blood pressure sound component of the two microphone signals is reduced;

(c) least means square filtering the microphone signal sum; and (d) subtracting the least means square filtered microphone signal sum from each of the first and second microphone signals.

25. The method of claim 20 wherein the selected maximum wave width value is less than a minimum wave width of a blood pressure sound.

26. The method of claim 20 wherein the first noise signal threshold level adjustment coefficient is larger than the second noise signal threshold level adjustment coefficient.

27. The method of claim 20 wherein the step of applying pressure to the artery includes the step of inflating an inflatable cuff wrapped around an arm of the patient, and wherein the first and second microphones are placed on the arm of the patient under the inflatable cuff along an axis of the artery.

28. A method for detecting the blood pressure levels of a patient, comprising the steps of:

(a) placing a first microphone on the patient near the location of an artery, the first microphone producing a first microphone signal in response to blood pressure sounds and noise picked up by the first microphone;

(b) placing a second microphone on the patient near the location of the artery and separated a distance from the first microphone, the second microphone producing a second microphone signal in response to blood pressure sounds and noise picked up by the second microphone;

(c) applying pressure to the artery at a plurality of pressure levels ranging from above a systolic blood pressure level of the patient to below a diastolic blood pressure level of the patient, the artery being forced open during part of the heart beat cycle when the patient's blood pressure exceeds the pressure applied to the artery, the opening of the artery causing a blood pressure sound to be produced;

(d) multiplying the first and second microphone signals to generate a microphone signal product;

(e) wave width filtering the microphone signal product to remove therefrom portions of the microphone signal product having a wave width which is less than a selected minimum wave width value to generate a wave width filtered blood pressure sound detection signal;

(f) comparing the wave width filtered blood pressure sound detection signal to a noise signal threshold level;

(g) indicating the detection of a blood pressure sound when the wave width filtered blood pressure sound detection signal exceeds the noise signal threshold level;

(h) repeating the steps of multiplying the first and second microphone signals, wave width filtering the microphone signal product, comparing the wave width filtered blood pressure sound detection signal to the noise signal threshold level, and indicating the detection of a blood pressure sound at each of the plurality of pressure levels; and (i) displaying a systolic blood pressure level of the patient as a highest of the plurality of pressure levels at which a blood pressure sound is indicated as being detected and displaying a diastolic blood pressure level of the patient as a lowest of the plurality of pressure levels at which a blood pressure sound is indicated as being detected.

29. The method of claim 28 wherein the step of applying pressure to the artery at a plurality of pressure levels includes the step of slowly reducing pressure in an inflatable cuff from above a maximum probable systolic blood pressure level of the patient to a pressure level below the diastolic blood pressure level of the patient.

30. The method of claim 28 wherein the second microphone is placed on the patient such that a center of the second microphone is separated a distance from a center of the first microphone such that a blood pressure sound picked up by the first microphone will be picked up out of phase by the second microphone.

31. The method of claim 28 comprising additionally the step of selecting portions of the first and second microphone signals having characteristics corresponding to blood pressure sounds before multiplying the first and second microphone signals.

32. The method of claim 31 wherein the step of selecting portions of the first and second microphone signals includes the step of filtering the first and second microphone signals with filters having pass bands corresponding approximately to the frequency range of blood pressure sounds.

33. The method of claim 31 wherein the step of selecting portions of the first and second microphone signals includes the steps of:

(a) gain controlling one of the first and second microphone signals to match the average levels of the first and second microphone signals;

(b) adding the microphone signals together to create a microphone signal sum in which a blood pressure sound component of the two microphone signals is reduced;

(c) least means square filtering the microphone signal sum; and (d) subtracting the least means square filtered microphone signal sum from each of the first and second microphone signals.

34. The method of claim 28 wherein the selected minimum wave width value is less than a minimum wave width of a blood pressure sound.

35. The method of claim 28 comprising additionally the steps of:

(a) wave width filtering the microphone signal product to remove therefrom portions of the microphone signal product having a wave width which is greater than a selected maximum wave width value to generate a wave width filtered noise amplitude signal;

(b) comparing the wave width filtered noise amplitude signal to the noise signal threshold level;

(c) increasing the noise signal threshold level by an amount related to the product of a first noise signal threshold level adjustment coefficient and a difference between the noise signal threshold level and the wave width filtered noise amplitude signal if the wave width filtered noise amplitude signal exceeds the noise signal threshold level; and (d) decreasing the noise signal threshold level by an amount related to the product of a second noise signal threshold level adjustment coefficient and the difference between the noise signal threshold level and the wave width filtered noise amplitude signal if the wave width filtered noise amplitude signal is less than the noise signal threshold level.

36. The method of claim 35 wherein the selected maximum wave width value is less than a minimum wave width of a blood pressure sound.

37. The method of claim 35 wherein the selected minimum wave width value and the selected maximum wave width value are equal.

38. The method of claim 35 wherein the first noise signal threshold level adjustment coefficient is larger than the second noise signal threshold level adjustment coefficient.

39. The method of claim 35 wherein the step of comparing the wave width filtered blood pressure sound detection signal to the noise signal threshold level is delayed from the steps of increasing or decreasing the noise signal threshold level such that the wave width filtered blood pressure sound detection signal based on the microphone signal product is compared to a noise signal threshold level which is increased or decreased based on a microphone signal product from a future point in time.

40. An apparatus for detecting blood pressure sounds in a patient, comprising:

(a) an inflatable cuff adapted to be wrapped around a limb of a patient;

(b) a first microphone fixed in the inflatable cuff, the first microphone producing a first microphone signal in response to blood pressure sounds and noise picked up by the first microphone;

(c) a second microphone fixed in the inflatable cuff and separated a distance from the first microphone, the second microphone producing a second microphone signal in response to blood pressure sounds and noise picked up by the second microphone;

(d) means for inflating the inflatable cuff to thereby apply pressure to the limb of the patient such that an artery in the patient's limb will be forced closed during part of a heart beat cycle and will be forced open during part of the heart beat cycle when the patient's blood pressure exceeds the pressure applied to the artery, the opening of the artery causing a blood pressure sound to be produced;

(e) means for multiplying the first and second microphone signals to generate a microphone signal product;

(f) means for wave width filtering the microphone signal product to remove therefrom portions of the microphone signal product having wave width which is less than a selected minimum wave width value to generate a wave width filtered blood pressure sound detection signal;

(g) means for comparing the wave width filtered blood pressure sound detection signal to a noise signal threshold level; and (h) means for indicating the detection of a blood pressure sound when the wave width filtered blood pressure sound detection signal exceeds the noise signal threshold level.

41. The apparatus for detecting blood pressure sounds of claim 40 wherein the second microphone is fixed in the inflatable cuff such that a center of the second microphone is separated a distance from a center of the first microphone such that a blood pressure sound picked up by the first microphone will be picked up out of phase by the second microphone.

42. The apparatus for detecting blood pressure sounds of claim 40 comprising additionally means for selecting portions of the first and second microphone signals having characteristics corresponding to blood pressure sounds before multiplying the first and second microphone signals.

43. The apparatus for detecting blood pressure sounds of claim 42 wherein the means for selecting portions of the first and second microphone signals includes band pass filters having pass bands corresponding approximately to a frequency range of blood pressure sounds.

44. The apparatus for detecting blood pressure sounds of claim 42 wherein the means for selecting portions of the first and second microphone signals includes:

(a) means for gain controlling one of the first and second microphone signals to match the average levels of the first and second microphone signals;

(b) means for adding the microphone signals together to create a microphone signal sum in which a blood pressure sound component of the two microphone signals is reduced;

(c) means for least means square filtering the microphone signal sum; and (d) means for subtracting the least means square filtered microphone signal sum from each of the first and second microphone signals.

45. The apparatus for detecting blood pressure sounds of claim 40 wherein the selected minimum wave width value is less than a minimum wave width of a blood pressure sound.

46. The apparatus for detecting blood pressure sounds of claim 40 comprising additionally:

(a) means for wave width filtering the microphone signal product to remove therefrom portions of the microphone signal product having a wave width which is greater than a selected maximum wave width value to generate a wave width filtered noise amplitude signal;

(b) means for comparing the wave width filtered noise amplitude signal to the noise signal threshold level;

(c) means for increasing the noise signal threshold level by an amount related to the product of a first noise signal threshold level adjustment coefficient and a difference between the noise signal threshold level and the wave width filtered noise amplitude signal if the wave width filtered noise amplitude signal exceeds the noise signal threshold level; and (d) means for decreasing the noise signal threshold level by an amount related to the product of a second noise signal threshold level adjustment coefficient and the difference between the noise signal threshold level and the wave width filtered noise amplitude signal if the wave width filtered noise amplitude signal is less than the noise signal threshold level.

47. The apparatus for detecting blood pressure sounds of claim 46 wherein the selected maximum wave width value is less than a minimum wave width of a blood pressure sound.

48. The apparatus for detecting blood pressure sounds of claim 46 wherein the selected minimum wave width value and the selected maximum wave width value are equal.

49. The apparatus for detecting blood pressure sounds of claim 46 wherein the first noise signal threshold level adjustment coefficient is larger than the second noise signal threshold level adjustment coefficient.

50. The apparatus for detecting blood pressure sounds of claim 40 wherein the means for multiplying the first and second microphone signals, the means for wave width filtering the microphone signal product, the means for comparing the wave width filtered blood pressure sound detection signal to a noise signal threshold level, and the means for indicating the detection of a blood pressure sound include a programmable microprocessor.

51. An apparatus for detecting the blood pressure levels of a patient, comprising:

(a) an inflatable cuff adapted to be wrapped around a limb of the patient;

(b) a first microphone fixed in the inflatable cuff, the first microphone producing a first microphone signal in response to blood pressure sounds and noise picked up by the first microphone;

(c) a second microphone fixed in the inflatable cuff and separated a distance from the first microphone, the second microphone producing a second microphone signal in response to blood pressure sounds and noise picked up by the second microphone;

(d) means for inflating and deflating the inflatable cuff to thereby apply pressure to the limb of the patient at a plurality of pressure levels ranging from above a systolic blood pressure level of the patient to below a diastolic blood pressure level of the patient, an artery in the patient's limb being forced open during part of the heart beat cycle when the patient's blood pressure exceeds the pressure applied to the limb, the opening of the artery causing a blood pressure sound to be produced;

(e) means for measuring the cuff pressure at each of the plurality of pressure levels;

(f) means for multiplying the first and second microphone signals to generate a microphone signal product;

(g) means for wave width filtering the microphone signal product to remove therefrom portions of the microphone signal product having a wave width which is less than a selected minimum wave width value to generate a wave width filtered blood pressure sound detection signal;

(h) means for comparing the wave width filtered blood pressure sound detection signal to a noise signal threshold level;

(i) means for indicating the detection of a blood pressure sound when the wave width filtered blood pressure sound detection signal exceeds the noise signal threshold level;

(j) means for multiplying the first and second microphone signals, wave width filtering the microphone signal product, comparing the wave width filtered blood pressure sound detection signal to the noise signal threshold level, and indicating the detection of a blood pressure sound at each of the plurality of pressure levels; and (k) means for displaying a systolic blood pressure level of the patient as a highest of the plurality of pressure levels at which a blood pressure sound is indicated as being detected and displaying a diastolic blood pressure level of the patient as a lowest of the plurality of pressure levels at which a blood pressure sound is indicated as being detected.

52. The apparatus for detecting blood pressure levels of claim 51 comprising additionally:

(a) means for wave width filtering the microphone signal product to remove therefrom portions of the microphone signal product having a wave width which is greater than a selected maximum wave width value to generate a wave width filtered noise amplitude signal;

(b) means for comparing the wave width filtered noise amplitude signal to the noise signal threshold level;

(c) means for increasing the noise signal threshold level by an amount related to the product of a first noise signal threshold level adjustment coefficient and a difference between the noise signal threshold level and the wave width filtered noise amplitude signal if the wave width filtered noise amplitude signal exceeds the noise signal threshold level; and (d) means for decreasing the noise signal threshold level by an amount related to the product of a second noise signal threshold level adjustment coefficient and the difference between the noise signal threshold level and the wave width filtered noise amplitude signal if the wave width filtered noise amplitude signal is less than the noise signal threshold level.

53. The apparatus for detecting blood pressure levels of claim 52 wherein the means for multiplying the first and second microphone signals, the means for wave width filtering the microphone signal product, the means for comparing the wave width filtered blood pressure sound detection signal to a noise signal threshold level, the means for indicating the detection of a blood pressure sound, the means for increasing the noise signal threshold level, and the means for decreasing the noise signal threshold level include a programmable microprocessor.

* * * * *